US009545424B2

(12) United States Patent
Amrein et al.

(10) Patent No.: US 9,545,424 B2
(45) Date of Patent: Jan. 17, 2017

(54) METHOD OF TREATING PULMONARY SURFACTANT DYSFUNCTION OR RESPIRATORY DISTRESS SYNDROME BY ADMINISTERING CYCLODEXTRIN OR A DERIVATIVE THEREOF

(71) Applicant: SolAeroMed Inc., Calgary (CA)

(72) Inventors: Matthias W. Amrein, Calgary (CA); Lasantha C. Gunasekara, Calgary (CA); Ryan Pratt, Mississauga (CA)

(73) Assignee: SolAero Med Inc., Calgary (CA)

( * ) Notice: Subject to any disclaimer, the term of this patent is extended or adjusted under 35 U.S.C. 154(b) by 0 days.

(21) Appl. No.: 13/629,474

(22) Filed: Sep. 27, 2012

(65) Prior Publication Data

US 2013/0029937 A1    Jan. 31, 2013

Related U.S. Application Data

(63) Continuation-in-part of application No. 12/628,544, filed on Dec. 1, 2009, now abandoned, which is a continuation of application No. PCT/EP2008/004274, filed on May 29, 2008.

(30) Foreign Application Priority Data

Jun. 1, 2007    (DE) .......................... 10 2007 025 898

(51) Int. Cl.

| A61K 31/724 | (2006.01) |
|---|---|
| A61K 45/06 | (2006.01) |
| A61K 47/48 | (2006.01) |
| A61K 35/42 | (2015.01) |
| B82Y 5/00 | (2011.01) |
| C08B 37/16 | (2006.01) |
| C08L 5/16 | (2006.01) |

(52) U.S. Cl.
CPC ............. *A61K 31/724* (2013.01); *A61K 35/42* (2013.01); *A61K 45/06* (2013.01); *A61K 47/48969* (2013.01); *B82Y 5/00* (2013.01); *C08B 37/0015* (2013.01); *C08L 5/16* (2013.01)

(58) Field of Classification Search
None
See application file for complete search history.

(56) References Cited

U.S. PATENT DOCUMENTS

2003/0171260 A1*   9/2003   Nelson .............................. 514/6

FOREIGN PATENT DOCUMENTS

| JP | 2008515847 A | 5/2008 |
|---|---|---|
| WO | 2006037769 A1 | 4/2006 |

OTHER PUBLICATIONS

Zidovetzki, R., & Levitan, I. (2007). Use of cyclodextrins to manipulate plasma membrane cholesterol content: evidence, misconceptions and control strategies. Biochimica et Biophysica Acta (BBA)—Biomembranes, 1768(6), 1311-1324.*
Lewis, J. F., & Veldhuizen, R. (2003). The role of exogenous surfactant in the treatment of acute lung injury. Annual review of physiology, 65(1), 613-642.*
Allen, G.B., et al. Neither Fibrin nor Plasminogen Activator Inhibitor-1 Deficiency Protects Lung Function in a Mouse Model of Acute Lung Injury. American Journal of Physiology—Lung Cellular and Molecular Physiology. 2009. pp. L277-L285. vol. 296.
Andersson, S., et al. Oxidative Inactivation of Surfactants. Lung. 1999. pp. 179. vol. 177.
Arnhold, J., et al. Formation of Lysophospholipids from Unsaturated Phosphatidylcholines under the Influence of Hypocholrous Acid. Biochimica Et Biophysica Acta (BBA)—General Subjects. 2002. pp. 91-100. vol. 1572.
Articas, G.R., et al. The American-European Consensus Conference on ARDS, Part 2: Ventilatory, Pharmacologic, Supportive Therapy, Study Design Strategies, and Issues Related to Recovery and Remodeling. American Journal of Respiratory and Critical Care Medicine. 1998. pp. 1332. vol. 157(1).
Bachofen, H., et al. Alveolar Surface Forces and Lung Architecture. Comparative Biochemistry and Physiology-Part A: Molecular & Integrative Physiology. 2001. pp. 183-193. vol. 129.
Bailey, T.C., et al. Physiological Effects of Oxidized Exogenous Surfactant in vivo: Effects of High Tidal Volume and Surfactant Protein A. American Journal of Physiology-Lung Cellular and Molecular Physiology. 2006. pp. L703-L709. vol. 291.
Baoukina, S., et al. The Molecular Mechanism of Lipid Monolayer Collapse. Proceedings of the National Academy of Sciences. 2008. pp. 10803. vol. 105.
Bernard, G.R., et al. Report of the American-European Consensus Conference on ARDS: Definitions, Mechanisms, Relevant Outcomes, and Clinical Trial Coordination. American Journal of Respiratory and Critical Care Medicine. 1994. pp. 72-81. vol. 149.

(Continued)

*Primary Examiner* — Shaojia Anna Jiang
*Assistant Examiner* — Dale R Miller
(74) *Attorney, Agent, or Firm* — Bennett Jones LLP

(57) ABSTRACT

The invention relates to a method for enhancing a surfactant, in particular a pulmonary surfactant, as well as a method for producing a surfactant enhancement agent, in particular a pulmonary surfactant enhancement agent. The invention also relates to a surfactant enhancement agent and a use of an enhancement agent for enhancing a surfactant, in particular, a pulmonary surfactant. Further, the invention relates to a method of mitigating oxidative damage to pulmonary surfactant by adding a cholesterol-sequestrating agent such as cyclodextrin. Finally, a method is provided for treating a patient having surfactant dysfunction due to oxidative damage to pulmonary surfactant by administering a surfactant-protective amount of a cholesterol-sequestrating agent to protect the surfactant from the negative effects of oxidative degradation. In the examples we show that MβCD, a cholesterol-sequestrating agent, can restore dysfunctional surfactant removed from the lungs of children with cystic fibrosis and non CF bronchiolitis to normal function.

13 Claims, 4 Drawing Sheets

(56) References Cited

OTHER PUBLICATIONS

Capote, K.R., et al. Pulmonary Surfactant Protein-A (SP-A) Restores the Surface Properties of Surfactant After Oxidation by a Mechanism that Requires the Cys6 Interchain Disulfide Bond and the Phospholipid Binding Domain. Journal of Biological Chemistry. 2003. pp. 20461. vol. 278.

Chabot, F., et al. Reactive Oxygen Species in Acute Lung Injury. European Respiratory Journal. 1998. pp. 745-757. vol. 11.

Chintagari, N.R., et al. Effect of Cholesterol Depletion on Exocytosis of Alveolar Type II Cells. American Journal of Respiratory Cell and Molecular Biology. 2006. pp. 677-687. vol. 34(6).

Christian, A.E., et al. Use of Cyclodextrins for Manipulating Cellular Cholesterol Content. Journal of Lipid Research. 1997. pp. 2264-2272. vol. 38.

Ciencewicki, J., et al. Oxidants and the Pathogenesis of Lung Diseases. Journal of Allergy and Clinical Immunology. 2008. pp. 456-468. vol. 122.

Clements, J. Surface Phenomena in Relation to Pulmonary Function. Physiologist. 1962. pp. 11. vol. 5.

Devendra, R.G., et al. Lung Surfactant in Subacute Pulmonary Disease. Respiratory Research. 2002. pp. 19. vol. 3.

Duck-Chong, C.G. A Rapid Sensitive Method for Determining Phospholipid Phosphorus Involving Digestion with Magnesium Nitrate. Lipids. 1979. pp. 492-497. vol. 14.

Fromming, K.H. Cyclodextrine. Deutsche Apotheker Zeitung. 1987. pp. 2040-2044. vol. 127(41).

Gilliard, G.P., et al. Exposure of the Hydrophobic Components of Porcine Lung Surfactant to Oxidant Stress Alters Surface Tension Properties. Journal of Clinical Investigation. 1994. pp. 2608. vol. 93.

Griese, M., et al. Pulmonary Surfactant, Lung Function, and Endobronchial Inflammation in Cystic Fibrosis. American Journal of Respiratory and Critical Care Medicine. 2004. pp. 1000-1005. vol. 170.

Griese, M., et al. Airway Inflammation in Children with Tracheostomy. Pediatric Pulmonology. 2004. pp. 356-361. vol. 37.

Gunasekara, L., et al. Pulmonary Surfactant Function is Abolished by an Elevated Proportion of Cholesterol. Biochimica et Biophysica Acta 2005. pp. 27-35. vol. 1737.

Gunasekara, L., et al. A Comparative Study of Mechanisms of Surfactant Inhibition. Biochimica et Biophysica Acta—Biomembranes. 2008. pp. 433-444. vol. 1778.

Gunasekara, L., et al. Methyl-[beta]-cyclodextrin Restores the Structure and Function of Pu.monary Surfactant Films Impaired by Cholesterol. Biochimica et Biophysica Acta—Biomembranes. 2010. pp. 986-994. vol. 1798.

Haddad, I.Y., et al. Mechanisms of Peroxynitrite-Induced Injury to Pulmonary Surfactants. American Journal of Physiology—Lung Cellular and Molecular Physiology. 1993. pp. L555-L564. vol. 265.

Haddad, I.Y., et al. Concurrent Generation of Nitric Oxide and Superoxide Damages Surfactant Protein A. American Journal of Physiology—Lung Cellular and Molecular Physiology. 1994. pp. L242-L249. vol. 267.

Haagsman, H.P., et al. Studies of the Structure of Lung Surfactant Protein SP-A. American Journal of Physiology—Lung Cellular and Molecular Physiology. 1989. pp. L421-L429. vol. 257.

Hudson, L.D., et al. Epidemiology of acute lung injury and ARDS. Chest. 1999. pp. 74S. vol. 116.

Jonson, B., et al. Pressure-Volume Curves and Compliance in Acute Lung Injury. American Journal of Respiratory and Critical Care Medicine. 1999. pp. 1172-1178. vol. 159.

Karagiorga, G., et al. Biochemical Parameters of Bronchoalveolar Lavage Fluid in Fat Embolism. Intensive Care Medicine. 2006. pp. 116-123. vol. 32.

Keating, E., et al. Effect of Cholesterol on the Biophysical and Physiological Properties of a Clinical Pulmonary Surfactant. Biophysical Journal. 2007. pp. 1391-1401. vol. 93.

Kolleck, I., et al. Cellular Cholesterol Stimulates Acute Uptake of Palmitate by Redistribution of Fatty Acid Translocase in Type II Pneumocytes. Biochemistry. 2002. pp. 6369-6375. vol. 41(20).

Lamb, N.J., et al. Oxidative Damage to Proteins of Bronchoalveolar Lavage Fluid in Patients with Acute Respiratory Distress Syndrome: Evidence for Neutrophil-Mediated Hydroxylation, Nitration, and Chlorination. Critical Care Medicine. 1999. pp. 1738. vol. 27.

Lang, J.D., et al. Oxidant-Antioxidant Balance in Acute Lung Injury. Chest. 2002. pp. 314S-320S. vol. 122.

Larsson, M. et al. The Bilayer Melting Transition in Lung Surfactant Bilayers: The Role of Cholesterol. European Biophysics Journal. pp. 633-636. vol. 31(8).

Leonenko, Z., et al. The Structure and Function of Molecular Films of Lung Surfactant: The Role of Cholesterol and Concentration. European Biophysics Journal. 2005. pp. 701. vol. 34(6).

Leonenko, Z., et al. Effect of Cholesterol on the Physical Properties of Pulmonary Surfactant Films: Atomic Force Measurements Study. 2006. pp. 687-694. vol. 106(8-9).

Leonenko, Z., et al. An Elevated Level of Cholesterol Impairs Self-Assembly of Pulmonary Surfactant into a Functional Film. Biophysical Journal. 2007. pp. 674-683. vol. 93.

Manzanares, D., et al. Modification of Tryptophan and Methionine Residues is Implicated in the Oxidative Inactivation of Surfactant Protein B. Biochemistry. 2007. pp. 5604-5615. vol. 46.

Mark, L., et al. Surfactant Function and Composition After Free Radical Exposure Generated by Transition Metals. American Journal of Physiology—Lung Cellular and Molecular Physiology. 1999. pp. L491. vol. 276.

Martin, T.R., Cytokines and the Acute Respiratory Distress Syndrome (ARDS): A Question of Balance. Nature Medicine. 1997. pp. 272. vol. 3.

Montgomery, M.A., et al. Causes of Mortality in Patients with the Adult Respiratory Distress Syndrome. American Review of Respiratory Disease. 1985. pp. 485. vol. 132.

Nahmen Von, A., et al. The Structure of a Model Pulmonary Surfactant as Revealed by Scanning Force Microscopy. Biophysical Journal. 1997. pp. 463-469. vol. 72.

Panda, A.K., et al. Effect of Acute Lung Injury on Structure and Function of Pulmonary Surfactant Films. American Journal of Respiratory Cell and Molecular Biology. 2004. pp. 641-650. vol. 30.

Possmayer, F., et al. Surface Activity in vitro: Role of Surfactant Proteins. Comparative Biochemistry and Physiology Part A: Molecular and Integrative Physiology. 2001. pp. 209-220. vol. 129.

Postle, A.D., et al. A Comparison of the Molecular Species Compositions of Mammalian Lung Surfactant Phospholipids. Comparative Biochemistry and Physiology Part A: Molecular and Integrative Physiology. 2001. pp. 65-73. vol. 129.

Rodriguez-Capote, D., et al. Reactive Oxygen Species Inactivation of Surfactant Involves Structural and Functional Alterations to Surfactant Proteins SP-B and SP-C. Biophysical Journal. 2006. pp. 2808. vol. 90.

Serrano, A.G., et al. Intrinsic Structural and Functional Determinants Within the Amino Acid Sequence of Mature Pulmonary Surfactant Protein SP-B. 2005. pp. 417-430. vol. 44.

Stenger, P.C., et al. Environmental Tobacco Smoke Effects on Lung Surfactant Film Organization. Biochimica et Biophysica Acta-Biomembranes. 2009. pp. 358-370. vol. 1788.

Tammi, R., et al. Localization of Epidermal Hyaluronic Acid Using the Hyaluronate Binding Region of Cartilage Proteoglycan as a Specific Probe. Journal of Investigative Dermatology. 1988. pp. 412-414. vol. 90.

Veldhuizen, R., et al. The Role of Lipids in Pulmonary Surfactant. Biochimica et Biophysica Acta-Molecular Basis of Disease. 1998. pp. 90-108. vol. 1408.

Vockeroth, D., et al. Role of Cholesterol in the Biophysical Dysfunction of Surfactant in Ventilator-Induced Lung Injury. American Journal of Physiology—Lung Cellular and Molecular Physiology. 2010. pp. L117-L125. vol. 298.

White, N.M., et al. Altered Cholesterol Homeostatis in Cultured and in vivo Models of Cystic Fibrosis. American Journal of Physiology—Lung Cellular and Molecular Physiology. 2007. pp. L476-L486. vol. 292.

Yu, S., et al. Bovine Pulmonary Surfactant: Chemical Composition and Physical Properties. 1983. pp. 522-529. vol. 18.

(56) References Cited

OTHER PUBLICATIONS

Yu, Y., et al. Molecular Dynamics Study of the Inclusion of Cholesterol into Cyclodextrins. The Journal of Physical Chemistry Pat B. 2006. pp. 6372-6376. vol. 110(12).

Zaas, et al. The Role of Lipid Rafts in the Pathogenesis of Bacterial Infections. Biochimica et Biophysica Acta—Molecular Cell Research. 2005. pp. 305-313. vol. 1746(3).

Zuo, Y.Y., et al. Current Perspectives in Pulmonary Surfactant-Inhibition, Enhancement and Evaluation. Biochimica et Biophysica Acta—Biomembranes. 2008. pp. 1947-1977. vol. 1778.

R. Buccoliero et al: "Elevation of lung surfactant phosphatidylcholine in mouse models of Sandhoff and of Niemann—Pick A disease", Journal of Inherited Metabolic Disease., vol. 27, No. 5, Sep. 1, 2004 (Sep. 1, 2004 ), pp. 641-648, XP55254195, NL ISSN: 0141-8955, DOI: 10.1023/B:BOLI.0000042958.22066.6c.

ICU and CCU, 1999, vol. 23, No. 5, pp. 323-331.

Japan Interface Medical Journal, vol. 30, 1999, pp. 20-28.

\* cited by examiner

FIGS. 1A and B
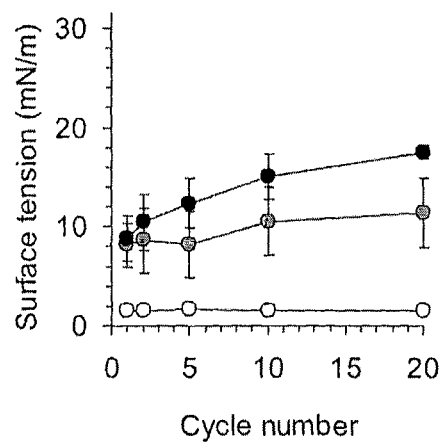
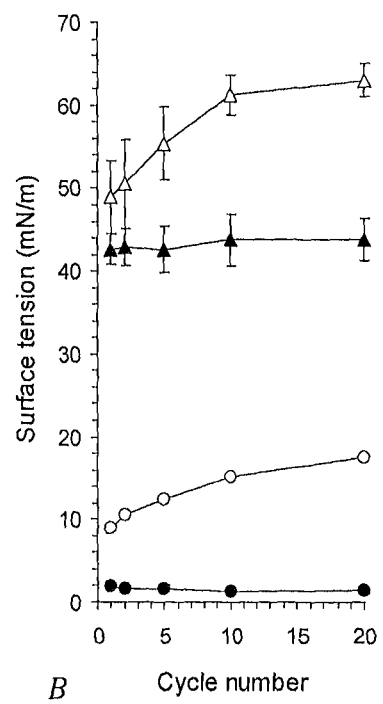

FIGS. 2A, B, C and D
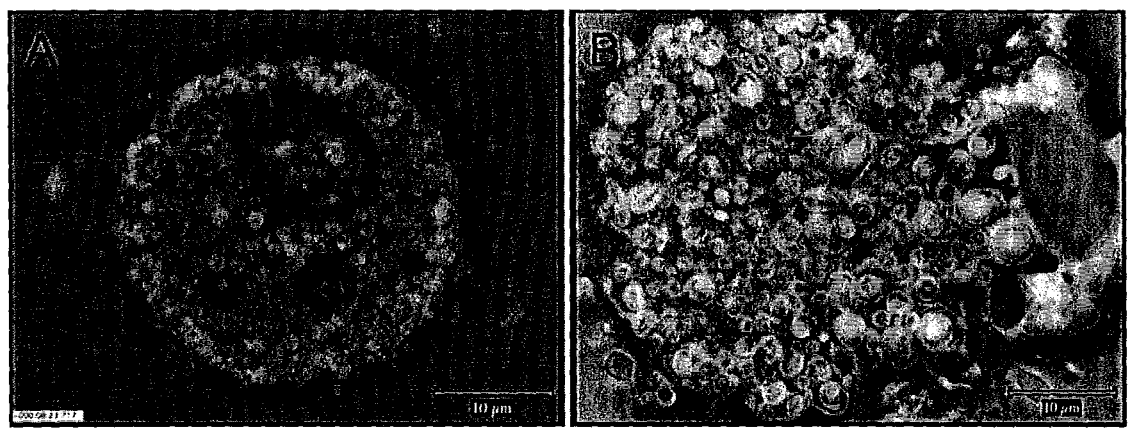
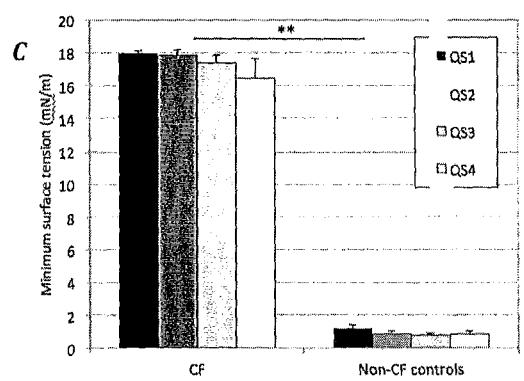
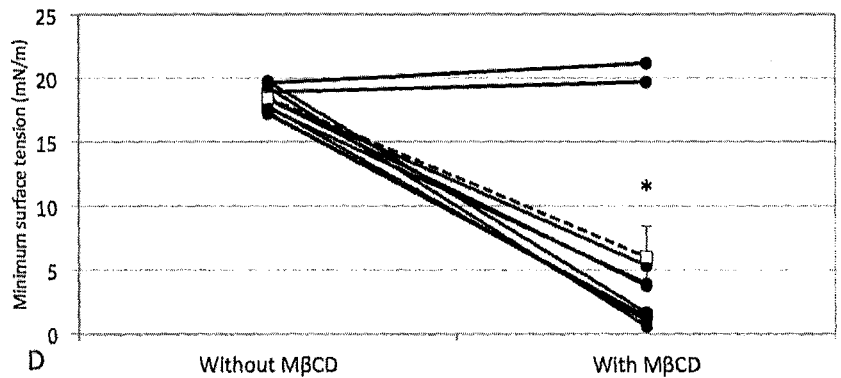

FIGS 3A, B, C, D and E
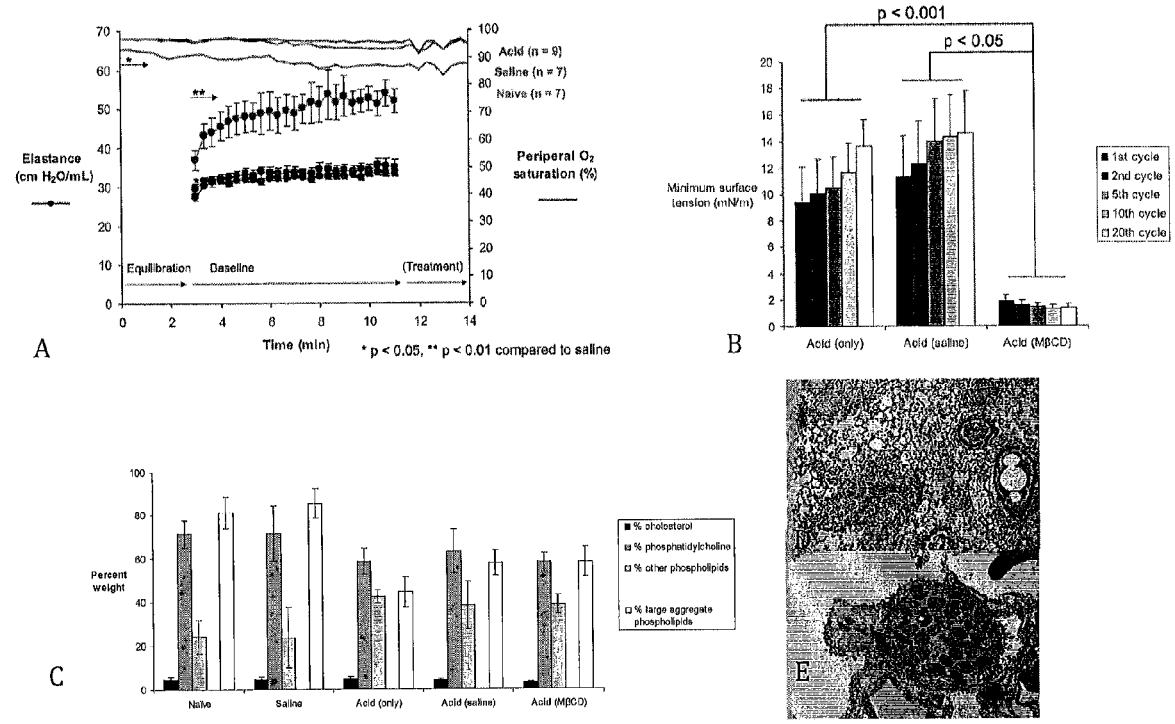

FIGS. 4A, B and C
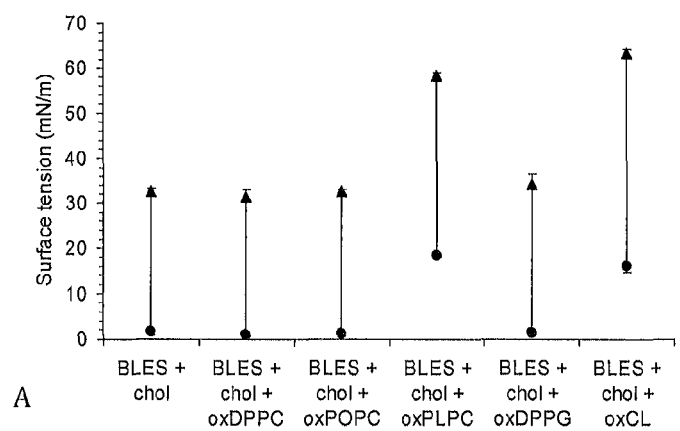
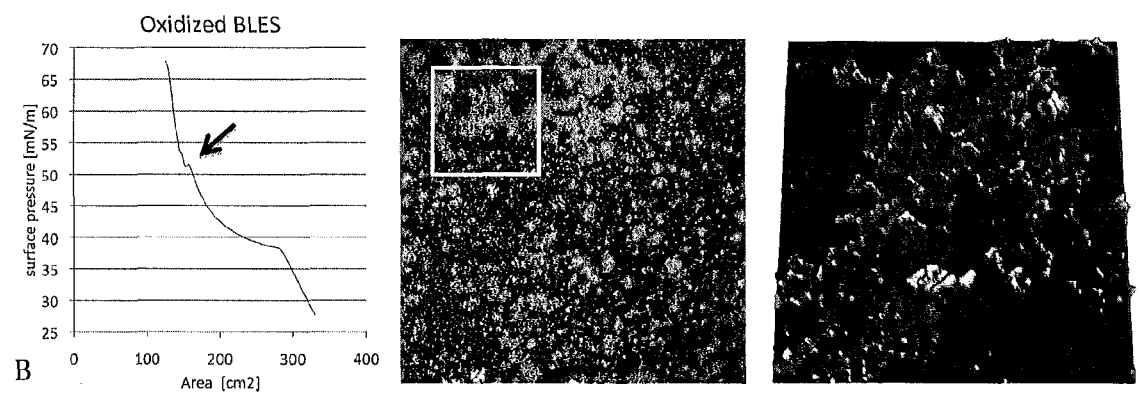
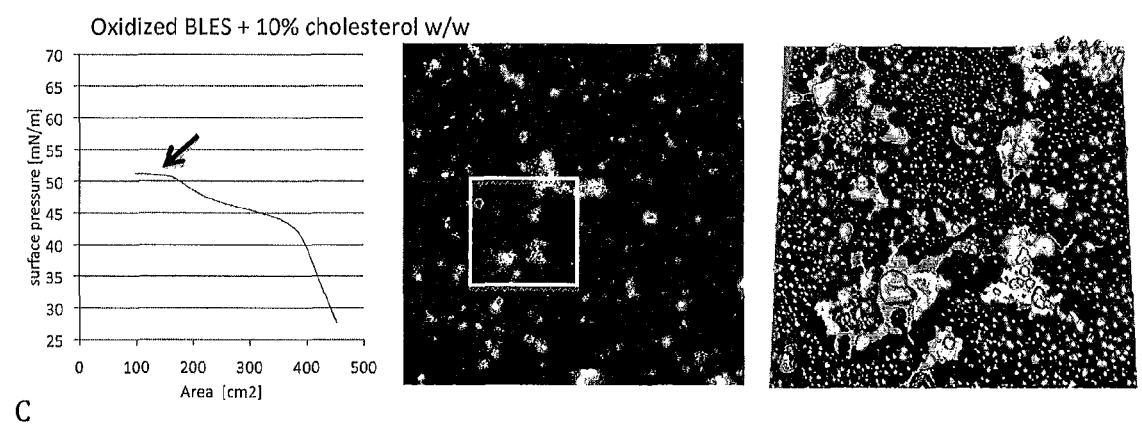

METHOD OF TREATING PULMONARY SURFACTANT DYSFUNCTION OR RESPIRATORY DISTRESS SYNDROME BY ADMINISTERING CYCLODEXTRIN OR A DERIVATIVE THEREOF

This application is a Continuation-in-Part of the National Phase filing under 35 U.S.C 371 of PCT Appl. No. PCT/EP2008/004274 filed May 29, 2008, which claims the benefit of German Application No. DE 10 2007025898 A1 filed on Jun. 1, 2007, both applications of which application are incorporated by reference herein in their entirety.

FIELD OF THE INVENTION

The invention relates to a method for enhancing a surfactant, in particular a pulmonary surfactant (also called lung surfactant), as well as a method for producing a surfactant enhancement agent, in particular a pulmonary surfactant enhancement agent. The invention also relates to a surfactant enhancement agent and a use of an enhancement agent for enhancing a surfactant, in particular, a pulmonary surfactant. Further, the invention relates to a method of mitigating oxidative damage to pulmonary surfactant by adding a cholesterol-sequestrating agent such as cyclodextrin. Finally, a method is provided for treating a patient having surfactant dysfunction due to oxidative damage to pulmonary surfactant by administering a surfactant-protective amount of a cholesterol-sequestrating agent to protect the surfactant from the negative effects of oxidative degradation.

BACKGROUND OF THE INVENTION

It is known that the pulmonary surfactant is a surface-active substance lining the respiratory system of the lung. Type II pneumocytes produce the surfactant, store it as lamellar bodies and finally express it in the alveolar liquid phase. From there it spreads as a molecular thin film on the air/water boundary surface. It displays its effect by dynamically adapting the surface tension of the boundary surface to the current extension of the boundary surface during the breathing cycle.

Pulmonary surfactant prevents alveolar collapse and flooding at end-expiration, affords patency of small airways and reduces the work required for breathing. Pulmonary surfactant consists of 80-90% (by weight) phospholipids, with a large proportion (~30-45%) being disaturated dipalmitoylphosphatidylcholine (DPPC). The surfactant also contains 50-60% unsaturated phospholipids with reported levels of polyunsaturated species >10% of total phospholipids. Surfactant also contains four surfactant-associated proteins—SP-A, B, C, and D. A highly surface-active form of pulmonary surfactant, referred to as the large aggregate fraction, is enriched in the hydrophobic proteins SP-B and SP-C. Neutral lipids, primarily cholesterol, make up the remaining 2-10% of surfactant.

In 1959 it was shown that the lack of pulmonary surfactant in the lungs of premature infants leads to respiratory distress syndrome (RDS), which at that time was the most frequent cause of death for premature infants. For about the past 15 years, extracts from the lungs of cattle or pigs have been used as a medication to treat RDS. Animal preparations are generally expensive and carry the risk of transmitting infectious diseases.

The surfactant (short for surface active agent) consists of glycero-phospholipids, specific proteins, neutral fats and cholesterol. The surfactant covers the alveolar surface and reduces the surface tension, so that after birth the alveoli do not collapse in the human body during exhalation.

Insufficient function of the surfactant can be the cause of respiratory insufficiency, known as Infant Respiratory Distress Syndrome (IRDS) in premature infants and newborns or in adults as Adult Respiratory Distress Syndrome (ARDS). These lung illnesses are the result of a surfactant deficiency, which lead to an inadequate expansion of the lungs (atelectasis) after a collapse of the pulmonary alveoli.

The lung surfactant consists of 90% lipids and 10% proteins. Although cooperation between the surfactant-specific proteins and the lipids is necessary for a completely functional respiratory process, the lipids are essential for the vitally important reduction of surface tension.

The function of pulmonary surfactants and their inhibited function with pulmonary infections and pulmonary diseases have been described in numerous publications. In this regard reference is made to the publications:

T. R. Martin, Cytokines and the Acute Respiratory Distress Syndrome (ARDS): a question of balance, Nat. Med. 3 (1997), pp. 272.

Artigas, G. R. Bernard, J. Cadet, D. Dreyfuss, L. Gattinoni, The American-European consensus conference on ARDS, part 2: ventilatory, pharmacologic, supportive therapy, study design strategies, and issues related to recovery and remodeling. Acute respiratory distress syndrome, Am. J. Respir. Crit. Care Med. 157 (Pt 1) (1998), pp. 1332.

G. R. Bernard, A. Artigas, K. L. Brigham, J. Carlet, K. Falke, The American-European consensus conference on ARDS: definitions, mechanisms, relevant outcomes, and clinical trial coordination, Am. J. Respir. Crit. Care Med. 149 (1994), pp. 818.

A. B. Montgomery, M. A. Stager, C. J. Carrico, E. D. Hudson, Causes of mortality in patients with the adult respiratory distress syndrome, Am. Rev. Respir. Dis. 132 (1985), pp. 485.

G. Karagiorga, G. Nakos, E. Galiatsou, M. E. Lekka, Biochemical parameters of bronchoalveolar lavage fluid in fat embolism, Intensive Care Medicine 32 (2006), pp. 116-123.

L. D. Hudson, K. P. Steinberg, Epidemiology of acute lung injury and ARDS, Chest 116 (1999), pp. 74S.

G. Devendra, R. G. Spragg, Lung surfactant in subacute pulmonary disease, Respir. Res. 3 (2002), pp. 19.

M. Griese, R. Essl, R. Schmidt, E. Rietschel, F. Ratjen, M. Ballmann, K. Paul, Pulmonary surfactant, lung function, and endobronchial inflammation in cystic fibrosis, American Journal Of Respiratory And Critical Care Medicine 170 (2004), pp. 1000-1005.

M. Griese, L. Felber, K. Reiter, R. Strong, K. Reid, B. H. Belohradsky, G. Jager, T. Nicolai, Airway inflammation in children with tracheostomy, Pediatr. Pulmonol. 37 (2004), pp. 356-361

Bachofen H & Schürch S (2001) Alveolar surface forces and lung architecture. *Comparative Biochemistry and Physiology—Part A: Molecular & Integrative Physiology* 129: 183-193.

Clements J (1962) Surface phenomena in relation to pulmonary function. *Physiologist* 5: 11.

Yu S, Harding P G, Smith N & Possmayer F (1983) Bovine pulmonary surfactant: Chemical composition and physical properties. *Lipids* 18: 522-9.

Veldhuizen R, Nag K, Orgeig S & Possmayer F (1998) The role of lipids in pulmonary surfactant. *Biochimica Et Biophysica Acta (BBA)—Molecular Basis of Disease* 1408: 90-108.

Yu S, Harding P G R, Smith N & Possmayer F (1983) Bovine pulmonary surfactant: Chemical composition and physical properties. *Lipids* 18: 522-529.

Postle A D, Heeley E L & Wilton D C (2001) A comparison of the molecular species compositions of mammalian lung surfactant phospholipids. *Comparative Biochemistry and Physiology—Part A: Molecular & Integrative Physiology* 129: 65-73.

Possmayer F, Nag K, Rodriguez K, Qanbar R & Schurch S (2001) Surface activity in vitro: Role of surfactant proteins. *Comp Biochem Physiol A Mol Integr Physiol* 129: 209-20.

Pulmonary surfactants form a complex film, which has or plays a critical role in the reduction of surface tension in the respiratory tract in the hydrated air/lung interface. With inflammatory lung diseases, the molecular profile of pulmonary surfactants in the alveoli and respiratory tract is changed so that the pulmonary surfactant film is quite a lot less effective or ineffective for reducing the surface tension, which is accompanied by a strong decrease in the area available for gas exchange.

Furthermore, it is known that an elevated level of cholesterol in the surfactants is a major cause of surfactant dysfunction. In this regard reference is also made to the following publication:

L. Gunasekara, S. Schurch, W. M. Schoel, K. Nag, Z. Leonenko, M. Haufs, M. Amiein, Pulmonary surfactant function is abolished by an elevated proportion of cholesterol, Biochimica Et Biophysica Acta 1737 (2005), 27-35.

Furthermore, it has been shown that the release of reactive oxygen species (ROS) from activated leukocytes or following exposure to environmental pollutants may result in a highly oxidizing milieu within the lungs. Increased levels of reactive oxygen species and their byproducts have been detected from bronchoalveolar lavage fluid collected from patients with ARDS, asthma, CF, ventilator induced lung injury (VILI) or chronic obstructive pulmonary disease (COPD), among many other disease states. Several studies have shown that oxidation of various pulmonary surfactants greatly impairs in vitro and in vivo function, which has so far been largely attributed to oxidative alterations of susceptible residues in SP-B and SP-C, whereas peroxidation and hydrolysis of phospholipids were considered less important. In this regard reference is also made to the following publications:

K. Rodriguez-Capote, D. Manzanares, T. Haines, F. Possmayer, Reactive oxygen species inactivation of surfactant involves structural and functional alterations to surfactant proteins SP-B and SP-C, Biophysical Journal 90 (2006), 2808.

S. Andersson, A. Kheiter, T. A. Merritt, Oxidative inactivation of surfactants, Lung 177 (1999), 179.

L. Mark, E. P. Ingenito, Surfactant function and composition after free radical exposure generated by transition metals, Am. J. Physiol.—lung Cell. Mol. Physiol. 276 (1999), L491.

N. Gilliard, G. P. Heldt, J. Loredo, H. Gasser, H. Redl, T. A. Merritt, R. G. Spragg, Exposure of the hydrophobic components of porcine lung surfactant to oxidant stress alters surface tension properties, Journal Of Clinical Investigation 93 (1994), 2608.

Lang J D, McArdle P J, O'Reilly P J & Matalon S (2002) Oxidant-antioxidant balance in acute lung injury*. *Chest* 122: 314S-320S.

Ciencewicki J, Trivedi S & Kleeberger S R (2008) Oxidants and the pathogenesis of lung diseases. *J Allergy Clin Immunol* 122: 456-468.

Lamb N J, Gutteridge J, Baker C, Evans T W & Quinlan G J (1999) Oxidative damage to proteins of bronchoalveolar lavage fluid in patients with acute respiratory distress syndrome: Evidence for neutrophil-mediated hydroxylation, nitration, and chlorination. *Crit. Care Med* 27: 1738.

Andersson S, Kheiter A & Merritt T (1999) Oxidative inactivation of surfactants. Lung 177: 179-189.

Bailey T C, et al (2006) Physiological effects of oxidized exogenous surfactant in vivo: Effects of high tidal volume and surfactant protein A. *American Journal of Physiology—Lung Cellular and Molecular Physiology* 291: L703-L709.

Gilliard N, et al (1994) Exposure of the hydrophobic components of porcine lung surfactant to oxidant stress alters surface tension properties. *J Clin Invest* 93: 2608.

Haddad I Y, et al (1993) Mechanisms of peroxynitrite-induced injury to pulmonary surfactants. *American Journal of Physiology—Lung Cellular and Molecular Physiology* 265: L555-L564.

Mark L & Ingenito E (1999) Surfactant function and composition after free radical exposure generated by transition metals. *American Journal of Physiology—Lung Cellular and Molecular Physiology* 276: L491-L500.

Stenger P C, et al (2009) Environmental tobacco smoke effects on lung surfactant film organization. *Biochimica Et Biophysica Acta (BBA)—Biomembranes* 1788: 358-370.

Rodriguez-Capote K, Manzanares D, Haines T & Possmayer F (2006) Reactive oxygen species inactivation of surfactant involves structural and functional alterations to surfactant proteins SP-B and SP-C. *Biophys J* 90: 2808-2821.

Manzanares D, et al (2007) Modification of tryptophan and methionine residues is implicated in the oxidative inactivation of surfactant protein B. *Biochemistry* 46: 5604-5615.

Keating E, et al (2007) Effect of cholesterol on the biophysical and physiological properties of a clinical pulmonary surfactant. *Biophys J* 93: 1391-1401.

This invention addresses the unaddressed question concerning the contribution of cholesterol to oxidation-induced surfactant dysfunction. In particular, it remained unknown, until this invention; whether oxidative alterations to surfactant interact with normal or increased levels of cholesterol to negatively affect surfactant function.

SUMMARY OF THE INVENTION

One aspect of the present invention relates to enhancing surfactants in a simple manner, in particular pulmonary surfactants, which, for example, are inhibited by cholesterol and exhibit dysfunction, where in particular the surface tension of the inhibited surfactants is improved by the treatment.

More particularly, a method for enhancing a surfactant is provided, in particular a pulmonary surfactant, which is further established in that the surfactant is enhanced with a cholesterol sequestrating surfactant enhancement agent, wherein given, in particular cholesterol of the surfactant is selectively sequestrated by means of the surfactant enhancement agent, such that the effect of cholesterol on the surfactant is reduced or reversed and thus also the dysfunction of the surfactant triggered by cholesterol.

In another aspect, a method for treating a patient having surfactant dysfunction due to exposure to reactive oxygen species (ROS) and their derivatives is provided comprising administering to the patient a surfactant-protective amount of a cholesterol sequestrating agent to protect the surfactant from the negative effects of oxidative damage by ROS.

Examples of ROS include, but are not limited to, superoxide and hydroxyl radicals. An example of a ROS derivative is peroxynitrite. In another aspect, a method for treating a patient having pulmonary surfactant dysfunction due to oxidative damage to pulmonary surfactant is provided comprising administering to the patient a surfactant-protective amount of a cholesterol-sequestrating agent to protect the surfactant from negative effects of oxidative degradation.

In yet a further aspect, a method of mitigating oxidative damage to pulmonary surfactant by adding a cholesterol-sequestrating agent such as cyclodextrin is provided. In one embodiment, protecting a surfactant from free radical damage due to oxidization of polyunsaturated phospholipids is provided comprising adding to the surfactant a surfactant-protective amount of a cholesterol sequestrating agent.

It was discovered that at the concentrations of cholesterol sequestrating agent used herein, oxidized, cholesterol-depleted surfactant exhibited few defects in surface activity. However, when such surfactants contain physiological levels of cholesterol, severe dysfunction is observed in terms of ability to reach low surface tensions upon compression, efficient film re-spreading upon expansion, and rapid interfacial film formation. Among the many biochemical effects of surfactant oxidation, lipid peroxidation was necessary for dysfunction. ROS are part of most inflammatory lung diseases. For most of these cases, cholesterol levels are not, or not substantially, elevated. Accordingly, a treatment of cholesterol dependent surfactant dysfunction by ROS is applicable to a much broader patient population than the treatment of an elevation of surfactant cholesterol.

For example, but not limiting, the present invention may be useful in treating patients suffering from acute lung injury (ALI) or acute respiratory distress syndrome (ARDS) from causes including shock, bacterial, viral and nosocomial pneumonias, ventilator-induced lung injury (VILI), aspiration, systemic inflammatory response syndrome (SIRS) or inhalation of toxic gases, vapors, fumes and particles. Also, the present invention is useful where the patient is suffering from airway injury including asthma, cystic fibrosis (CF), chronic obstructive pulmonary disease (COPD) or inhalation of toxic gases, vapors, fumes and particles or a patient with infant respiratory distress syndrome (IRDS) that is not responding to treatment or Niemann-Pick disease.

BRIEF DESCRIPTION OF THE DRAWINGS

FIG. 1A shows minimum surface tensions during cycles for oxidized BLES with 0% (white), 5% (grey), or 10% (black) cholesterol. This model system shows that oxidation in the absence of cholesterol does not affect normal surfactant function. In the presence of cholesterol, the function is lost and surface tension high for oxidized surfactant * $p<0.05$, ** $p<0.01$ FIG. 1B shows minimum (circles) and maximum (triangles) surface tensions during dynamic compression-expansion cycles of oxBLES+10% w/w cholesterol in control buffer (white) or buffer containing 30 mM MβCD (black). Thus, oxidized cholesterol containing surfactant is dysfunctional in vitro and its function can be restored by a cholesterol-sequestrating agent.

FIG. 2A is a light micrograph of an alveolar macrophage in the BAL fluid of a CF patient (Bar=10 μm). Numerous lipid-containing lysosomes are in the cytoplasm.

FIG. 2B shows that excessive engorgement of surfactant leads to immotile macrophages and eventually the disruption of the plasma membrane.

FIG. 2C shows surfactant testing. CF samples show high surface tension (dysfunction) vs functional controls (results are displayed in minimum surface tensions reached during consecutive expansion-compression cycle of the CBS).

FIG. 2D shows that MβCD restores CF patients' surfactant function in vitro. * $p<0.05$, ** $p<0.01$.

FIG. 3A shows that elastance is increased and oxygenation decreased for injured mice.

FIG. 3B shows surfactant is dysfunctional (minimum surface tension >10 mN/m) for untreated injured mice but normal if injured mice were treated with an MβCD-aerosol (minimum tension <10 mN/m).

FIG. 3C shows surfactant cholesterol is not elevated for injured mice.

FIG. 3D shows histological lung sections that show a pronounced influx of neutrophils in injury.

FIG. 3E shows an EM micrograph that shows increased surfactant (membranous inclusions) in type II alveolar epithelium cells in injury.

Hence, FIGS. 3A-E show surfactant dysfunction for an animal model of ALI and its restoration by a cholesterol-sequestrating agent given as an aerosol in vivo.

FIG. 4A shows minimum and maximum surface tensions during dynamic cycle 20 with BLES+10% w/w cholesterol, additionally containing 20% w/w oxDPPC, oxPOPC, oxPLPC, oxDPPG, or oxCL.

FIG. 4B shows Langmuir-isotherm, left, fluorescence micrograph (middle, 50 μm×50 μm) and AFM topography, right, (15 μm×15 μm, as outlined in the fluorescence micrograph) of surfactant films as indicated. Black in fluorescence- and dark maroon in the AFM images represent areas of lipid monolayer, homogenous grey or light maroon indicates areas of lipid bilayers. For oxidized BLES, a mostly normal isotherm, coincides with a mostly normal film structure of a lipid monolayer (black in fluorescence, dark maroon in AFM) interspersed with areas of lipid bilayers (grey and light maroon, respectively). Some film collapse seen in the isotherm (arrow) corresponds to irregular lipid micelles seen in fluorescence as bright spots and in AFM as irregular protrusions.

FIG. 4C shows oxidized surfactant containing also cholesterol shows a collapse plateau in the isotherm (arrow). In fluorescence and the AFM, bilayer regions are scarce and large lipid collapse structures abundant (white).

Thus, FIGS. 4A-C show that polyunsaturated phospholipids in surfactant are responsible for the above described dysfunction. It also shows that the mechanism of the defect at the structural level.

DETAILED DESCRIPTION

In the context of the invention, the term "lipid sequestrating" or "cholesterol sequestrating" is understood to mean that lipids or cholesterol of a surfactant are removed from the surfactant in their particularly dysfunctional effect and/or are inhibited in their effect on the surfactant and/or act on the surfactant as a medium which makes lipids soluble in order to reduce or reverse the aforementioned inhibitory effect of the lipids and/or cholesterol. The surfactant dysfunction particularly occurs if there is an increased cholesterol level in the surfactant.

Through the action of the sequestrating surfactant enhancement agent, the dysfunction of the surfactant triggered by the cholesterol as a result of elevated cholesterol content above the corresponding normal level of cholesterol in the surfactants, is at least partially to entirely nullified as well as at least partially to completely reversed.

Lipid sequestrating or cholesterol sequestrating enhancement agents to be considered here are those media which particularly correspond to the action or active substance class of cyclodextrin, in particular of methyl-β-cyclodextrin, on a surfactant and/or a pulmonary surfactant. In this way, for example, the inhibiting effect of cholesterol on a surfactant is weakened or nullified.

Through the inventive enhancement of the surfactant, in particular endogenous surfactant, it is furthermore possible, for example, that a cholesterol-induced or a cholesterol-dependent inhibiting effect on the surfactant can be diagnosed. In addition to that, the properties of the surfactant can also be influenced or modified accordingly by the surfactant enhancement agent, which enables pulmonary diseases, in particular acute pulmonary diseases and chronic pulmonary diseases, to be treated. Examples of acute pulmonary illnesses are acute lung injury (ALI), ARDS, acute respiratory insufficiency, pneumonias, particularly ventilator-induced lung injuries, nosocomial infections or systemic inflammatory response syndrome (SIRS) associated with ALI and bronchiolitis. Chronic lung diseases are for example cystic fibrosis, asthma, chronic obstructive pulmonary disease (COPD) and Niemann-Pick disease.

Through the use of a cholesterol sequestrating surfactant enhancement agent, the surfactant is correspondingly influenced in its surface-active properties, so that the surface activity of endogenous, treated pulmonary surfactants can be determined, for instance, using a captive bubble surfactometer, for example.

Moreover, the method is distinguished in that the surfactant is enhanced using a surfactant enhancement agent containing cyclodextrin or using a surfactant enhancement agent corresponding in action to a surfactant enhancement agent containing cyclodextrin or to the activity class of cyclodextrin.

Furthermore, an embodiment is envisaged in which an active substance of the surfactant enhancement agent methyl-β-cyclodextrin (MβCD) or cyclodextrin, especially 2-hydroxypropyl-β-cyclodextrin, or cyclodextrin derivatives which have 2-hydroxypropyl-β-cyclodextrin in particular, is present or dipalmitoylphosphatidylcholine (DPPC) or corresponding derivates of the aforementioned substances or a mixture of the substances mentioned or at least a lipid-selective and lipid-deactivating substance or at least a lipid-sequestrating substance are used.

In particular, the surface tension of the surfactant is reduced by the surfactant enhancement agent compared to an unenhanced surfactant or compared to the surfactant before enhancement.

In addition to that, it is envisaged in an embodiment that cholesterol of the surfactant is dissolved and/or passivated by the surfactant enhancement agent in a solution, particularly an aqueous solution. In this manner the inhibiting effect of cholesterol of the surfactant, for example on its surface activity, is treated accordingly. Consequently the surface activity and/or the surface tension of surfactants can be determined and diagnosed easily subsequent to enhancement.

Furthermore it is envisaged according to one embodiment that the surfactant enhancement agent sequestrate cholesterol of the surfactant which have an effect, particularly an inhibiting one, on the properties of the surfactant, especially the unenhanced surfactant, or which limit its properties.

In addition to that the object is solved by a method for producing a surfactant enhancement agent, in particular a pulmonary surfactant enhancement agent, which is further developed in that at least a portion of at least a cholesterol-selective and at least a cholesterol-sequestrating substance will be or is mixed with the surfactant enhancement agent.

Preferably at least one substance will be or is mixed with the surfactant enhancement agent through which with the application on a surfactant, preferably an endogenous surfactant, cholesterol which have an effect, particularly an inhibiting one, on the properties of the surfactant, especially the unenhanced surfactant, or which limit its properties, are sequestrated.

Furthermore, in accordance with the invention, the surfactant enhancement agent is mixed with an active substance constituted by methyl-β-cyclodextrin (MβCD) or cyclodextrin, especially 2-hydroxypropyl-β-cyclodextrin, or cyclodextrin derivatives which have 2-hydroxypropyl-β-cyclodextrin in particular, or dipalmitoylphosphatidylcholine (DPPC) or corresponding derivates of the aforementioned substances or a mixture of the substances mentioned or at least a cholesterol-selective and cholesterol-deactivating substance or at least a cholesterol-sequestrating substance.

In addition to that, the surfactant enhancement agent can also contain other materials and/or active substances without loss of the aforementioned action of the sequestrating substance, i.e. the effect of this sequestrating substance is or will be retained. For example, during administration as a medication or pharmaceutical, another surfactant, for example an exogenously acting surfactant, can be added to the surfactant enhancement agent.

Furthermore, the object is solved by a surfactant enhancement agent, which is further developed in that at least a portion of at least a lipid-selective and lipid-deactivating substance or at least a lipid-sequestrating substance or cholesterol-sequestrating substance will be or is mixed with the surfactant enhancement agent.

Furthermore, the surfactant enhancement agent is distinguished in that with the use of the surfactant enhancement agent, i.e. during enhancement of a surfactant, the surfactant will be or is enhanced using the surfactant enhancement agent which has as an active substance methyl-β-cyclodextrin (MβCD) or cyclodextrin, especially 2-hydroxypropyl-β-cyclodextrin, or cyclodextrin derivatives which have 2-hydroxypropyl-β-cyclodextrin in particular, or dipalmitoylphosphatidylcholine (DPPC) or corresponding derivates of the aforementioned substances or a mixture of the substances mentioned or at least a cholesterol-selective and cholesterol-deactivating substance or at least a cholesterol-sequestrating substance.

In particular, the surface tension of the surfactant will be or is reduced with the use of the surfactant enhancement agent compared to an unenhanced surfactant or compared to the surfactant before enhancement.

Preferably cholesterol of the surfactant are dissolved and/or passivated by the surfactant enhancement agent in a solution, in particular an aqueous solution.

In addition to that it is envisaged that with the use of the surfactant enhancement agent, cholesterol of the particularly endogenous surfactant which have an effect, particularly an inhibiting one, on the properties of the surfactant, especially the unenhanced surfactant, or which limit its properties will be or are sequestrated by the surfactant enhancement agent.

Moreover, the invention is solved by the use of an enhancement agent for enhancing a surfactant, in particular an endogenous surfactant, in particular a pulmonary surfactant, in which the enhancement agent is or will be made according to the process described above, or in which the surfactant enhancement agent is made from the constituents described above. For this purpose, to avoid repetition, explicit reference is made to the information above.

Advantageously, the application is distinguished in that the enhancement agent is used as a therapeutic agent or pharmaceutical for treating pulmonary illnesses in living beings, in particular humans. For example, the enhancement agent can be present as a pharmaceutical in powder form for exhalative administration or in liquid form for intra-tracheal or intra-bronchial administration. Beyond that in a further development it is possible that the enhancement agent be used with patients in aerosol form. Administration ensues in a manner known to the specialist, preferably by intra-tracheal instillation of a solution or suspension or in the form of an atomized solution or suspension or by atomization of powder.

Furthermore, the object is solved by the use of methyl-β-cyclodextrin (MβCD) or cyclodextrin, in particular 2-hydroxypropyl-β-cyclodextrin, or cyclodextrin derivatives which have 2-hydroxypropyl-β-cyclodextrin in particular, or dipalmitoylphosphatidylcholine (DPPC) or corresponding derivates of the aforementioned substances or a mixture of the substances mentioned or at least a cholesterol-selective and cholesterol-deactivating substance or at least a cholesterol-sequestrating substance, whereby cholesterol of a surfactant is sequestrated, in particular for the production of pharmaceuticals for the treatment or early treatment of pulmonary illnesses in humans, in particular acute pulmonary illnesses.

Furthermore, the object is solved by the use of methyl-β-cyclodextrin (MβCD) or cyclodextrin, in particular 2-hydroxypropyl-β-cyclodextrin, or cyclodextrin derivatives which have 2-hydroxypropyl-β-cyclodextrin in particular, or dipalmitoylphosphatidylcholine (DPPC) or corresponding derivates of the aforementioned substances or a mixture of the substances mentioned or at least a cholesterol-selective and cholesterol-deactivating substance or at least a cholesterol-sequestrating substance, whereby cholesterol of a surfactant is sequestrated, in particular for the investigation, in particular diagnosis, of surfactants, in particular pulmonary surfactants.

In the context of the invention is furthermore possible that by the sequestrating effect of the surfactant enhancement agent the dysfunction will be reduced with respect to the surface tension of a surfactant, in particular an endogenous surfactant, whereby after corresponding enhancement of the surfactant the dysfunction is diminished or nullified by an increased level of cholesterol or lipids in the surfactant.

The invention is based on the idea that a use of methyl-β-cyclodextrin (MβCD) or other cyclodextrin or other cholesterol-sequestrating substances in the activity class or the active substance class of cyclodextrin, including dipalmitoylphosphatidylcholine (DPPC), and a use of substances corresponding to the activity class of cyclodextrin, which reverse or nullify the effect(s) of cholesterol by others means, including vitamin E, as agents makes it possible not only to diagnose or determine the effected or induced inhibition of the surfactant by cholesterol but also to treat the effected or induced inhibition of the surfactant by cholesterol in patients or people with the aforementioned symptoms or those with effected or induced inhibition of the surfactant by cholesterol.

For the enhancement of the symptoms described, the substance or active substance can be delivered to the lung in aerosol form or instilled in the lung as a substance together with at least one exogenous, i.e. externally acting surfactant or delivered to the lung in another manner.

As a means of diagnosis, the inventive substance can be mixed with a specimen of a surfactant from a patient, the function of which is subsequently checked in a surface balance. Alternatively, the substance can be added to an aqueous solution or an aqueous phase of a surface balance to determine the function of the surfactants.

These results and findings were obtained on the basis of systems of model surfactants and pulmonary surfactants of CF patients and ARDS-patients. They will be explained below based on two examples.

In another aspect, the present application shows that severe inhibition of surfactant by oxidation is cholesterol-dependent. Without being bound to theory, it is believed that the mechanism of surfactant dysfunction demonstrated in vitro herein is relevant to diseases. Studies in which oxidized surfactants have been instilled into various animal models have shown good associations between in vitro performance and in vivo activity (Bailey T C, et al (2006) Physiological effects of oxidized exogenous surfactant in vivo: Effects of high tidal volume and surfactant protein A. *American Journal of Physiology—Lung Cellular and Molecular Physiology* 291: L703-L709; Gilliard N, et al (1994) Exposure of the hydrophobic components of porcine lung surfactant to oxidant stress alters surface tension properties. *J Clin Invest* 93: 2608).

Moreover, the conditions for dysfunction found in vitro are met in multiple respiratory pathologies. Alveolar oxidative stress is associated with the pathogenesis of, among other diseases, ARDS, asthma, CF, and COPD (Ciencewicki J, Trivedi S & Kleeberger S R (2008) Oxidants and the pathogenesis of lung diseases. *J Allergy Clin Immunol* 122: 456-468). ROS likely originate to a substantial degree from activated immune cells and/or environmental sources in these diseases (Ciencewicki J, Trivedi S & Kleeberger S R (2008) Oxidants and the pathogenesis of lung diseases, *J Allergy Clin Immunol* 122: 456-468; Lamb N J, Gutteridge J, Baker C, Evans T W & Quinlan G J (1999) Oxidative damage to proteins of bronchoalveolar lavage fluid in patients with acute respiratory distress syndrome: Evidence for neutrophil-mediated hydroxylation, nitration, and chlorination. *Crit. Care Med* 27: 1738). As well, there are no reports of a decrease of cholesterol in inflammatory lung diseases. To the contrary, cholesterol in surfactant is increased in ARDS (Panda A. K., et al (2004) Effect of acute lung injury on structure and function of pulmonary surfactant films. *Am. J. Respir. Cell Mol. Biol.* 30: 641-650; Tammi R, Ripellino J A, Margolis R U & Tammi M (1988) Localization of epidermal hyaluronic acid using the hyaluronate binding region of cartilage proteoglycan as a specific probe. *J Invest Dermatol* 90: 412-414) and CF (our unpublished results). For these pathologies, the increased level of cholesterol can even explain the dysfunction on its own (Gunasekara L C, et al (2010) Methyl-[beta]-cyclodextrin restores the structure and function of pulmonary surfactant films impaired by cholesterol. *Biochimica Et Biophysica Acta (BBA)—Biomembranes* 1798: 986-994; Vockeroth D, et al (2010) Role of cholesterol in the biophysical dysfunction of surfactant in ventilator-induced lung injury. *American Journal of Physiology—Lung Cellular and Molecular Physiology* 298: L117-L125).

To ensure relevance to disease states, in the Examples below, attempts were made to match surfactant concentration, rate of compression-expansion, surfactant composition, and levels of oxidant exposure to known physiological or pathological parameters. However, by using lipid-extracted surfactants, we removed water-soluble endogenous anti-oxidant molecules present in natural surfactants that may render these more resistant to oxidation (Haddad I Y, et al (1993) Mechanisms of peroxynitrite-induced injury to pulmonary surfactants. *American Journal of Physiology—Lung*

Cellular and Molecular Physiology 265: L555-L564). For example, hyaluronic acid in the alveolar fluid possesses free-radical scavenging properties (Tammi R, Ripellino J A, Margolis R U & Tammi M (1988) Localization of epidermal hyaluronic acid using the hyaluronate binding region of cartilage proteoglycan as a specific probe. *J Invest Dermatol* 90: 412-414). On the other hand, surfactant in the inflamed lung could be subject to dilution by alveolar oedema and conversion of LA material into poorly surface-active small aggregates (reviewed in Zuo Y Y, Veldhuizen R A W, Neumann A W, Petersen N O & Possmayer F (2008) Current perspectives in pulmonary surfactant—inhibition, enhancement and evaluation. *Biochimica Et Biophysica Acta (BBA)—Biomembranes* 1778: 1947-1977; Tammi R, Ripellino J A, Margolis R U & Tammi M (1988) Localization of epidermal hyaluronic acid using the hyaluronate binding region of cartilage proteoglycan as a specific probe. *J Invest Dermatol* 90: 412-414), which may enhance oxidative dysfunction. Reactive oxygen species may also enhance the reactivity of reactive nitrogen species found in vivo, which are capable of further damaging surfactant lipids and proteins (Haddad I Y, et al (1993) Mechanisms of peroxynitrite-induced injury to pulmonary surfactants. *American Journal of Physiology—Lung Cellular and Molecular Physiology* 265: L555-L564; Haddad I Y, et al (1994) Concurrent generation of nitric oxide and superoxide damages surfactant protein A. *American Journal of Physiology—Lung Cellular and Molecular Physiology* 267: L242-L249).

EXAMPLES

Example 1

In a model study, 0, 5 and 10 weight percent cholesterol was added to a ROS-exposed cattle lipid surfactant extract as an example of how even a normal (physiological) amount of cholesterol renders surfactant exposed to ROS and its derivatives dysfunctional; the function of the surfactant model was determined in a captive bubble surfactometer (CBS).

In the absence of methyl-β-cyclodextrin (MβCD) (FIG. 1A), i.e. with unenhanced surfactant, the surface tension remained nearly unchanged near the equilibrium at 23 mN/m indicating severe surfactant is dysfunction.

In the presence of methyl-β-cyclodextrin (MβCD) (20 mmol) (FIG. 1B), i.e. with enhanced surfactant, in the aqueous phase the surfactant regained its normal function and the surface tension receded to almost zero.

Example 2

In this study with pediatric CF surfactant samples (n=10, FIG. 2 A-D), we found a high level of surfactant dysfunction. Cholesterol in the bronchoalveolar lavage BAL was increased to 17.6±6.2 wt % compared to lung-healthy control samples (5.5±0.9 wt %; n=5), who also showed normal surfactant function (FIG. 2C). When CF surfactant was re-tested in the presence of MβCD, a majority (8/10) of samples now showed restored function (FIG. 2D), suggesting that cholesterol was responsible for the dysfunction. The high cholesterol is explained by a CF-specific defect in cholesterol homeostasis (White, N. M. et al. Altered cholesterol homeostasis in cultured and in vivo models of cystic fibrosis. Am. J. Physiol.—Lung Cell. Mol. Physiol. 292, L476-L486 (2007)). On the other hand, five non-CF bronchiolitis surfactant samples from children were also dysfunctional and their function was also restored by MβCD despite normal cholesterol levels (5.6±0.5 wt %). The latter may be explained by our invention, namely, that degradation by reactive oxygen species (ROS) rendered surfactant dysfunctional in the presence of even normal levels of cholesterol. ROS are largely produced in the inflamed lung by neutrophils (Chabot, F., Mitchell, J., Gutteridge, J. & Evans, T. Reactive oxygen species in acute lung injury. European Respiratory Journal 11, 745-757 (1998)). Consistent with a role for neutrophils in surfactant dysfunction, the CF and non-CF bronchiolitis cases with dysfunction had increased neutrophils in their BAL fluid. We conclude the inflammatory environment primarily affects the non-CF bronchiolitis surfactant. By contrast there would appear to be a genetic component in CF, in addition to an inflammatory one. Both types of abnormality can be corrected with the cholesterol-binding agent MβCD, according to our preliminary data.

Example 3

In this study, a murine model of acute lung injury (ALI), the earliest phase of ARDS, was created by acid injury of the lung according to published procedures (Allen, G. B. et al. Neither fibrin nor plasminogen activator inhibitor-1 deficiency protects lung function in a mouse model of acute lung injury. American Journal of Physiology-Lung Cellular and Molecular Physiology 296, L277-L285 (2009)) and analyzed with respect to lung mechanics, oxygenation, lung histology, lung ultrastructure, surfactant function and composition (FIGS. 3A-E). Elastance (or its inverse, compliance) and pressure-volume curves are commonly used to assess lung function in ALI/ARDS (JONSON, B. et al. Pressure-volume curves and compliance in acute lung injury. American journal of respiratory and critical care medicine 159, 1172-1178 (1999)). Our initial data with this model shows cholesterol-dependent surfactant dysfunction despite physiologically normal levels of cholesterol (and an otherwise normal lipid profile), similar to the human non-CF bronchiolitis-cases and further supporting a mechanism whereby surfactant exposed to the oxidizing milieu of inflammation will fail in the presence of cholesterol. Importantly, we show that MβCD can restore surfactant function not only in vitro but also in vivo in the lung when given as an aerosol (FIG. 3B).

Example 4

In this Example, the role of oxidized polyunsaturated phospholipids in causing cholesterol-dependent surfactant dysfunction was studied. Oxidation of surfactant by the Fenton-like reaction or in the presence of ROS in the inflamed lung results in the formation of lipid-peroxides with polyunsaturated phospholipids the principal target. Lipid peroxides, while otherwise unaltered, possess a hydroperoxide group in their aliphatic tail(s). This introduction of a hydrophilic group in the formerly hydrophobic region will disrupt lipid packing. Addition of 20% w/w oxPLPC or oxCL to BLES+10% cholesterol caused substantial deterioration in surface activity (FIG. 4A). This effect was cholesterol-dependent, as oxPLPC or oxCL alone did not impair the surface activity of native BLES. BLES containing cholesterol and either PLPC or CL, while not initially inhibited, became dysfunctional after several hours possibly as a result of spontaneous oxidation by exposure to ambient air. This is consistent with peroxidized PLPC, CL and other polyunsaturated phospholipids present in surfactant causing dysfunction together with cholesterol. These results are of further interest given the finding of an important role for CL in surfactant dysfunction associated with pneumonia. In support of this interpretation, there was no inhibition produced by the addition of oxidation-exposed, non-polyunsaturated phospholipid species, and the addition of oxDPPC, oxDPPG, or oxPOPC to BLES+10% cholesterol did not negatively affect dynamic surface activity compared to controls. Lipid peroxidation depends on multiple double bonds in the aliphatic tail, and DPPC, DPPG or POPC are therefore not targets for this molecular alteration.

Polyunsaturated phospholipid species in addition to forming peroxides are also highly susceptible to oxidant-initiated hydrolysis. As a control, removal of the phospholipid hydrolysis products (as described above) from BLES+10% cholesterol containing oxPLPC or oxCL did not improve surface activity (not shown), thereby excluding the possibility that inhibition was due to the generation and incorporation of large quantities of lysophospholipids and FFAs. In summary, oxidized polyunsaturated phospholipids in conjunction with cholesterol render surfactant dysfunctional with the respective peroxides of the affected lipids being the most likely deleterious molecular species.

Example 5

Effects of oxidation on the structure of surfactant films was also studied. Low surface tension results from the surfactant forming an incompressible film at the air-buffer interface. In mechanical analogy, surface tension is equivalent to an external lateral pressure compressing a plate and the molecular film at the interface is the continuum plate. If functional, the film will not yield to the lateral pressure and thus offset the surface tension. If dysfunctional, the film will collapse by flowing off the interface into the buffer for fluid films. Rigid dysfunctional films will respond to the pressure by buckling if ductile or cracking if brittle.

Microscopy of Langmuir-Blodgett films (films formed at the air-buffer interface and then transferred onto a solid support) reveals important aspects of how pulmonary surfactant performs its function and how it fails. In the Atomic Force Microscope (AFM), oxBLES films show a pattern of monolayer areas and lipid bilayer regions (FIG. 4B, right). FIG. 4B, middle, is a fluorescence light micrograph of the film with the AFM-area outlined. From comparison, the bright regions are lipid bilayers. We and others found earlier that this pattern is a hallmark of functional films and results from a monolayer-bilayer conversion during compression (Leonenko, Z. et al. An elevated level of cholesterol impairs self-assembly of pulmonary surfactant into a functional film. Biophys. J. 93, 674-683 (2007); Baoukina, S., Monticelli, L., Risselada, H. J., Marrink, S. J. & Tieleman, D. P. The molecular mechanism of lipid monolayer collapse. Proceedings of the National Academy of Sciences 105, 10803 (2008); Serrano, A. G., Cruz, A., Rodriguez-Capote, K., Possmayer, F. & Perez-Gil, J. Intrinsic structural and functional determinants within the amino acid sequence of mature pulmonary surfactant protein SP-B. Biochemistry 44, 417-430 (2005); Nahmen von, A., Schenk, M., Sieber, M. & Amrein, M. The Structure of a Model Pulmonary Surfactant as Revealed by Scanning Force Microscopy. Biophys. J. 72, 463-469 (1997). The bilayer regions accommodate fluid, unsaturated lipids otherwise incompatible with low surface tension. The monolayer will thus be enriched in domains of saturated lipids (mostly DPPC) that allow for dense packing and low surface tension.

The bilayer stacks are cross-linked to the monolayer by the surfactant proteins B and C. We proposed earlier that these act as a mechanical re-enforcement preventing buckling or cracking of the film (Leonenko, Z. et al. An elevated level of cholesterol impairs self-assembly of pulmonary surfactant into a functional film. Biophys. J. 93, 674-683 (2007)). OxBLES, in contrast to untreated BLES, shows an additional abundance of globular extrusions of sub-micrometer dimensions, possibly representing micelles of defective lipids that have been squeezed out of the active film without compromising its overall performance.

FIG. 4B, left, is the area-surface pressure isotherm of the film, showing a shoulder at a film pressure between 35 and 40 mN/m, followed by a rise to a high surface pressure. Note that for the Langmuir trough, the film pressure $\Pi$ is recorded as opposed to the CBS, where surface tension $\gamma$ is measured; the two entities are related as $\Pi = \gamma_0 - \gamma$ with $\gamma_0$ being the surface tension of a free air-water interface of $\approx 70$ mN/m). The isotherm too is characteristic of functional surfactant, with the shoulder being caused by the monolayer-bilayer conversion (Leonenko, Z. et al. An elevated level of cholesterol impairs self-assembly of pulmonary surfactant into a functional film. Biophys. J. 93, 674-683 (2007)). A region of instability at about 50 mN/m (arrow), not seen with un-oxidized films, may indicate the expulsion of damaged lipids seen in the AFM topography as small protrusions. For oxBLES also containing cholesterol, bilayer areas are always associated with micrometer-sized globular matter, being the collapse structures of this dysfunctional film (FIG. 4C). Fluorescence images show a much smaller area of the interface covered by bilayers. In the isotherm a continuous collapse plateau at 50 mN/m reveals the dysfunction of the film.

In summary, oxidized surfactant in the absence of cholesterol maintains the functional structure of a lipid monolayer with an abundance of regions of lipid bilayers. AFM shows cholesterol in oxidized surfactant to affect most prominently the assembly of bilayers, resulting in large globular collapse structures in this region. This finding is consistent with bilayer regions that fail to mechanically re-enforce the film but rather become the foci from where lipids are lost to the aqueous phase.

Example 6

Methods and Experimental Procedures

Materials—BLES was a kind gift from BLES Biochemicals Inc. (London, ON, Canada). 1,2-dipalmitoyl-sn-glycerol, 1,2-dioleoyl-sn-glycerol, 1-palmitoyl-2-oleoyl-sn-glycero-3-phosphocholine (POPC), 1-palmitoyl-2-linoleoyl-sn-glycero-3-phosphocholine (PLPC), and bovine heart cardiolipin (CL, predominantly 1',3'-Bis[1,2-dilinoleoyl-sn-glycero-3-phospho]-sn-glycerol) were purchased from Avanti Polar Lipids Inc. (Alabaster, Ala., USA). All other chemicals were purchased from Sigma-Aldrich (St. Louis, Mo., USA). Human SP-A (hSP-A) was isolated from the whole lung lavage of a patient with alveolar proteinosis using butanol extraction as described by Haagsman et al. (Haagsman H P, et al (1989) Studies of the structure of lung surfactant protein SP-A. *American Journal of Physiology—Lung Cellular and Molecular Physiology* 257: L421-L429). The purity of this preparation was assessed by polyacrylamide gel electrophoresis followed by Coomassie blue staining. All lipids were stored at $-20°$ C. under nitrogen. Surfactant mixtures were stored at $4°$ C. under nitrogen and used within three days after preparation. Buffers containing HEPES were stored in the dark at $4°$ C. to avoid inadvertently generating $H_2O_2$ (Haddad I Y, et al (1993) Mechanisms of peroxynitrite-induced injury to pulmonary surfactants, *American Journal of Physiology—Lung Cellular and Molecular Physiology* 265: L555-L564).

In Vitro Oxidation—BLES was exposed to hydroxyl radicals generated from Fenton-like chemistry for 24 h to produce oxidized BLES (oxBLES) (as described by Rodriguez-Capote et al., Rodriguez-Capote K, Manzanares D, Haines T & Possmayer F (2006) Reactive oxygen species inactivation of surfactant involves structural and functional alterations to surfactant proteins SP-B and SP-C. *Biophys J* 90: 2808-2821; and Capote K R, McCormack F X & Possmayer F (2003) Pulmonary surfactant protein-A (SP-A) restores the surface properties of surfactant after oxidation by a mechanism that requires the Cys6 interchain disulfide bond and the phospholipid binding domain. *J Biol Chem* 278: 20461). DPPC, POPC, PLPC, DPPG, and CL were suspended in saline with 1.5 mM $CaCl_2$ and exposed to identical oxidizing conditions and are indicated as oxDPPC, oxPOPC, oxPLPC, oxDPPG, and oxCL in order to indicate exposure to oxidative conditions only. Oxidation of surfactant phospholipids was confirmed by measuring the formation of the secondary lipoperoxidation products malondialdehyde (MDA) and 4-hydroxyalkenal (4-HAE) in 1.0 mg/mL oxBLES (BIOXYTECH LPO-586, OxisResearch, Burlingame, Calif., USA). oxBLES contained significantly more MDA and 4-HAE compared to control BLES (6.69±1.16 and 2.69±0.63 nmol MDA and 4-HAE/mg phospholipid respectively, n=6, p=0.014), consistent with previous studies using this Fenton reaction-like oxidation.

Surfactant Preparation—To ensure accurate mixing, additional lipids were added to lipid extracts of BLES or oxBLES as organic solutions. The mixtures were then dried under nitrogen and resuspended in CBS buffer (140 mM NaCl, 10 mM HEPES, 2.5 mM $CaCl_2$, pH 6.9) to a phospholipid concentration of 27 mg/mL. Phospholipid concentration was assessed using a phosphate assay (Gentaur Molecular Products, Kampenhout, Belgium) after liberation of free phosphate (Duck-Chong C G (1979) A rapid sensitive method for determining phospholipid phosphorus involving digestion with magnesium nitrate. *Lipids* 14: 492-497). Total phospholipid concentration was 96.8±6.8% (n=6) after lipid extraction and 98.6±11.1% (n=12) after oxidation. BLES contained 2.60% cholesterol (w/w phospholipids) as determined using an enzymatic assay for cholesterol (Amplex Red Cholesterol Assay, Invitrogen, Eugene, Oreg., USA). hSP-A was added to dried films when indicated to a final concentration of 5% (w/w phospholipids). In a subset of experiments, water soluble products of phospholipid hydrolysis (Gilliard N, et al (1994) Exposure of the hydrophobic components of porcine lung surfactant to oxidant stress alters surface tension properties. *J Clin Invest* 93: 2608; Arnhold J, Osipov A N, Spalteholz H, Panasenko O M & Schiller J (2002) Formation of lysophospholipids from unsaturated phosphatidylcholines under the influence of hypochlorous acid, *Biochimica Et Biophysica Acta (BBA)— General Subjects* 1572: 91-100) were removed by high-speed centrifugation of dilute surfactant mixtures (40 000 g×30 min×4° C.). The supernatant fluid was discarded and the pellet was resuspended to the initial volume of concentrated surfactant. After high-speed centrifugation, the concentration of phospholipids in oxBLES was 61.9±9.7% that of likewise treated BLES (n=3, p=0.034).

To obtain surfactant containing physiological levels of cholesterol, five female, 12-week old C57BL6 mice (Jackson Laboratories, Bar Harbour, Me., USA) housed in a pathogen-free animal care facility at the University of Calgary Health Sciences Center were humanely euthanized with an overdose of i.p. sodium pentobarbital. A tracheal cannula was surgically placed and three 0.5 mL aliquots of normal saline were used for bronchoalveolar lavage (BAL). BAL fluid was immediately centrifuged (400 g×10 minutes×4° C.) to remove cellular debris, and the large aggregate fraction was then isolated from the supernatant by high-speed centrifugation as described above. These fractions were pooled and lipid extracted to obtain mouse lipid extract surfactant (MLES). After drying, this pooled fraction was resuspended in saline with 1.5 mM $CaCl_2$ to a final concentration of 10 mg/mL phospholipids and subsequently exposed to oxidation as described above to obtain oxMLES. MLES contained 7.3±1.6% cholesterol (w/w phospholipids).

Surface Activity Assessment—Surface activity of surfactant was determined with a computer-controlled captive bubble surfactometer (CBS) as described in detail by Gunasekara et al. (Gunasekara L, Schoel W M, Schürch S & Amrein M W (2008) A comparative study of mechanisms of surfactant inhibition. *BBA—Biomembranes* 1778: 433-444), with two important changes: 1) A transparent capillary was used to deposit a ~1.0 µL bolus of 27 mg/mL surfactant near the air-buffer interface. The quantity and concentration of surfactant were chosen to minimize effects caused by insufficient surfactant or bulk phase adsorption. This amount of native BLES reliably reproduces minimum and maximum surface tensions as measured in situ at functional reserve capacity and total lung capacity (<1 mN/m and ~30 mN/m, respectively) (Bachofen H & Schtirch S (2001) Alveolar surface forces and lung architecture. *Comparative Biochemistry and Physiology—Part A: Molecular & Integrative Physiology* 129: 183-193). In a subset of experiments, a transparent capillary was used to deposit 54.0 µL of 0.5 mg/mL surfactant to assess differences in surfactant function caused by concentration. 2) A conditioning step was performed to ensure consistent surface activity in subsequent compression-expansion cycles. The bubble was first quasi-statically compressed to ~20% of the maximum volume and subsequently expanded to set minimum and maximum volumes. Afterwards, the bubble volume was dynamically cycled over the same volume range at a rate of 20 cycles/minute to condition the film. Four quasi-static cycles and a second set of dynamic cycles were carried out afterwards. Measurements of surface tension and interfacial area were made on this second series of cycles. The compressibility ratio at 20 mN/m ($C_{20}$) was calculated using the following formula: $C_{20}=(\delta A/\delta\gamma)/A$, where A=surface area and γ=surface tension.

To evaluate the effect of MβCD, powdered MβCD (Sigma Aldrich, Catalogue-Nr. C4555) was dissolved in buffer to a final concentration of 30 mM and added to the CBS chamber prior to the addition of surfactant. Calcium-free experiments were conducted using CBS buffer without calcium and with 15 mM EDTA added. Surfactants used in these experiments were incubated overnight in EDTA-containing buffer before use.

Isotherms and Film Deposition—Suspensions of bovine lipid extract surfactant (BLES) were compared with respect to surface activity on a Langmuir trough and surfactant structure as deduced by atomic force- and fluorescence light microscopy. Samples of a) oxBLES, b) oxBLES with 10% w/w cholesterol, and c) oxBLES with 10% w/w cholesterol and hSP-A were prepared as described above. A fluorescent lipid analogue (Rhodamine-DHPE, Invitrogen, Eugene, Oreg., USA) was added to a concentration of 0.1% mol/mol DPPC prior to aqueous suspension.

Surfactant suspensions were spread into a film at the air-buffer interface (750 cm²) of a Langmuir trough (Nima Technology, Coventry, UK) at 37° C. by placing a drop of approximately 10 μl (at a concentration of 27 mg/ml) at the interface. The film area was reduced at a rate of 100 cm$^2$/min from 600 cm$^2$ to 100 cm$^2$ and re-opened. This cycle was then repeated twice. The surface tension was continuously monitored and area-surface tension isotherm recorded. Next, the area was reduced again, until a surface pressure of 45 mN/m was achieved. At this point, films for microscopy were deposited onto round (25 mm) microscope cover slips by the Langmuir-Blodgett technique. For deposition, the previously submerged cover slip was moved perpendicular across the air-buffer interface at a speed of 25 mm/min while the surface tension was kept constant.

Microscopy—AFM topographical images were collected in air in intermittent contact mode with a NanoWizard II AFM (JPK Instruments, Berlin, Germany) using noncontact mode silicon cantilevers NCH-20 (NanoWorld, Neuchâtel, Switzerland) with typical spring constants of 21-78 N/m, and resonance frequencies of 260-460 kHz. The AFM was fitted on a Zeiss Axio Observer (Zeiss, Jena, Germany). Optical fluorescence images were acquired of sample regions containing the AFM scan regions using a Zeiss 40× Apoplan oil-immersion objective (numerical aperture: 1.4) and an Andor iXon EMCCD camera (Andor, Belfast, Ireland). The optical images were corrected for optical distortions and the magnification accurately calibrated by taking advantage of the AFM scanner to establish reference points (using the "optical overlay" feature of the AFM software). This allowed for an accurate overlay of the two imaging modes.

Statistical Analysis—All CBS experiments are reported as mean±SEM (n=4-7). Each unique lipid mixture was prepared independently at least twice. Analysis of variance (SPSS 19.0) between two groups was followed by Tukey's HSD for multiple comparisons with $p<0.05$ used as the standard for significance. Means with the same letter and case in a figure are not statistically different for that cycle.

In summary, oxidized surfactant in the absence of cholesterol maintains the functional structure of a lipid monolayer with an abundance of regions of lipid bilayers. AFM shows cholesterol in oxidized surfactant to affect most prominently the assembly of bilayers, resulting in large globular collapse structures in this region. This finding is consistent with bilayer regions that fail to mechanically re-enforce the film but rather become the foci from where lipids are lost to the aqueous phase.

Without being bound to theory, it is believed that surfactant dysfunction is caused by the combination of oxidation and cholesterol. We show for the first time that ROS lead to lipid peroxides that interact with cholesterol to induce instability in the bilayer regions of the surfactant films. The collapse structures seen in the Figures and the plateau of the isotherm (FIG. 4) suggest that the bilayer regions will continuously eject surfactant material at high film pressure. Oxidation also depletes surfactant of unsaturated phospholipids, which, in conjunction with the condensing effects of cholesterol, results in a poorly deformable film. This becomes apparent in the isotherm (FIG. 4) from an onset of the monolayer-bilayer conversion plateau at a film pressure above 50 mN/m, as opposed to 40 mN/m of functional films. At this point, the film might be brittle and prone to breaking, contributing to the progressive inability to reach low surface tensions with subsequent compression cycles.

We claim:

1. A method for treating a patient having pulmonary surfactant dysfunction due to oxidative damage to pulmonary surfactant, comprising administering to the patient a surfactant-protective amount of a cyclodextrin or derivative thereof to protect the surfactant from negative effects of oxidative degradation.

2. The method of claim 1, wherein the patient is suffering from acute lung injury (ALI), acute respiratory distress syndrome (ARDS) from causes including shock, bacterial, viral and nosocomial pneumonias, ventilator-induced lung injury (VILI), aspiration, systemic inflammatory response syndrome (SIRS) or inhalation of toxic gases, vapors, fumes and particles.

3. The method of claim 1, wherein the patient is suffering from airway injury including asthma, cystic fibrosis (CF), chronic obstructive pulmonary disease (COPD) or inhalation of toxic gases, vapors, fumes and particles, infant respiratory distress syndrome (IRDS) that is not responding to treatment, or Niemann-Pick disease.

4. The method of claim 1, wherein the cyclodextrin is methyl-β-cyclodextrin (MβCD) or derivatives thereof.

5. The method of claim 1, wherein the cyclodextrin is 2-hydroxypropyl- β-cyclodextrin or derivatives thereof.

6. The method of claim 1, wherein the oxidative damage is due to the presence of reactive oxygen species (ROS) or their derivatives.

7. The method of claim 6, wherein the ROS is a superoxide or a hydroxyl radical.

8. The method of claim 6, wherein the ROS derivative is peroxynitrite.

9. A method of treating a patient with a respiratory distress syndrome, wherein the pulmonary surfactant of said patient has a normal level of cholesterol, the method comprising the step of administering to the patient a composition comprising a therapeutically effective amount of a pulmonary surfactant comprising phospholipids and a cyclodextrin or derivatives thereof in an amount sufficient to sequester the cholesterol from any polyunsaturated phospholipids should the polyunsaturated phospholipids become oxidized in the lung.

10. The method of claim 9, wherein the cyclodextrin or derivatives thereof is methyl-β-cyclodextrin (MβCD) or derivatives thereof.

11. The method of claim 9, wherein the cyclodextrin or derivatives thereof is a 2-hydroxypropyl- β-cyclodextrin or derivatives thereof.

12. The method of claim 9, wherein the respiratory distress syndrome is acute lung injury (ALI), acute respiratory distress syndrome (ARDS) from causes including shock, bacterial, viral and nosocomial pneumonias, ventilator-induced lung injury (VILI), aspiration, systemic inflammatory response syndrome (SIRS) or inhalation of toxic gases, vapors, fumes and particles.

13. The method of claim 9, wherein the respiratory distress syndrome is asthma, cystic fibrosis (CF), chronic obstructive pulmonary disease (COPD) or inhalation of toxic gases, vapors, fumes and particles, infant respiratory distress syndrome (IRDS) that is not responding to treatment, or Niemann-Pick disease.

* * * * *